(12) United States Patent
Maehana et al.

(10) Patent No.: US 10,345,299 B2
(45) Date of Patent: Jul. 9, 2019

(54) METHOD FOR DETECTING COLIFORM BACTERIA CONTAINED IN MILK

(71) Applicant: ASAHI KASEI KABUSHIKI KAISHA, Tokyo (JP)

(72) Inventors: Koji Maehana, Tokyo (JP); Kenji Matsuyama, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 365 days.

(21) Appl. No.: 15/105,420

(22) PCT Filed: Dec. 17, 2014

(86) PCT No.: PCT/JP2014/083460
§ 371 (c)(1),
(2) Date: Jun. 16, 2016

(87) PCT Pub. No.: WO2015/093545
PCT Pub. Date: Jun. 25, 2015

(65) Prior Publication Data
US 2016/0320387 A1    Nov. 3, 2016

(30) Foreign Application Priority Data
Dec. 18, 2013   (JP) .................. 2013-261824

(51) Int. Cl.
*G01N 33/569* (2006.01)
*C12N 1/06* (2006.01)
*C12Q 1/04* (2006.01)

(52) U.S. Cl.
CPC ......... *G01N 33/56911* (2013.01); *C12N 1/06* (2013.01); *C12Q 1/04* (2013.01); *G01N 2333/195* (2013.01); *G01N 2469/00* (2013.01)

(58) Field of Classification Search
None
See application file for complete search history.

(56) References Cited

U.S. PATENT DOCUMENTS

| 5,786,208 A | 7/1998 | Clark et al. |
| 2010/0099115 A1 | 4/2010 | Mach et al. |
| 2010/0184210 A1* | 7/2010 | Rossmanith ............ C12Q 1/24 435/325 |

FOREIGN PATENT DOCUMENTS

| JP | 63-167799 A | 7/1988 |
| JP | 01-244370 | 9/1989 |

(Continued)

OTHER PUBLICATIONS

Atroshi et al., "Fat Globule Membrane of Sow Milk as a Target for Adhesion of K88-Positive *Escherichia coli*", Comp. Immun. Microbiol. Infect. Dis., vol. 6, No. 3 (1983) pp. 235-245.

(Continued)

*Primary Examiner* — Erik B Crawford
(74) *Attorney, Agent, or Firm* — Birch, Stewart, Kolasch & Birch, LLP

(57) ABSTRACT

The object is to provide a lysis method, lysis treatment solution, detection method using an immunochromatographic device, and detection kit comprising an immunochromatographic device for detecting whether causative bacteria of mastitis are coliform bacteria or not by using milk of a livestock animal. There is provided a method for lysing coliform bacteria, which comprises the step of mixing a lysis agent containing a lytic enzyme, and at least one kind of anionic surfactant, and preferably further containing at least one kind of nonionic surfactant, with milk obtained form a livestock animal to lyse coliform bacteria existing in the milk. The lytic enzyme is preferably lysozyme.

13 Claims, 2 Drawing Sheets

(56) References Cited

FOREIGN PATENT DOCUMENTS

| | | |
|---|---|---|
| JP | 07-196463 A | 8/1995 |
| JP | 9-505479 | 6/1997 |
| JP | 2003-505077 A | 2/2003 |
| JP | 2003-171291 | 6/2003 |
| JP | 2006258803 A | 9/2006 |
| JP | 2010-154851 A | 7/2010 |
| JP | 4621919 | 11/2010 |
| JP | 2012-122921 A | 6/2012 |
| JP | 2014-066641 A | 4/2014 |
| WO | WO 95/14768 A2 | 6/1995 |
| WO | WO 01/07599 A1 | 2/2001 |
| WO | WO 2005/064016 A1 | 7/2005 |
| WO | WO 2010/137624 A1 | 12/2010 |
| WO | WO 2011018858 A1 | 2/2011 |

OTHER PUBLICATIONS

International Preliminary Report on Patentability issued in International Application No. PCT/JP2014/083460 dated Jun. 30, 2016.
International Search Report issued in International Application No. PCT/JP2014/083460 dated Mar. 31, 2015.
Extended European Search Report, dated Jun. 19, 2017, for corresponding European Application No. 14870998.3.

\* cited by examiner

[Fig. 1]
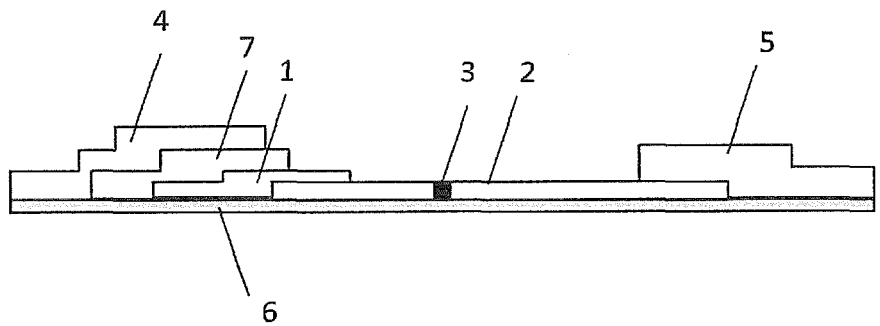
[Fig. 2]
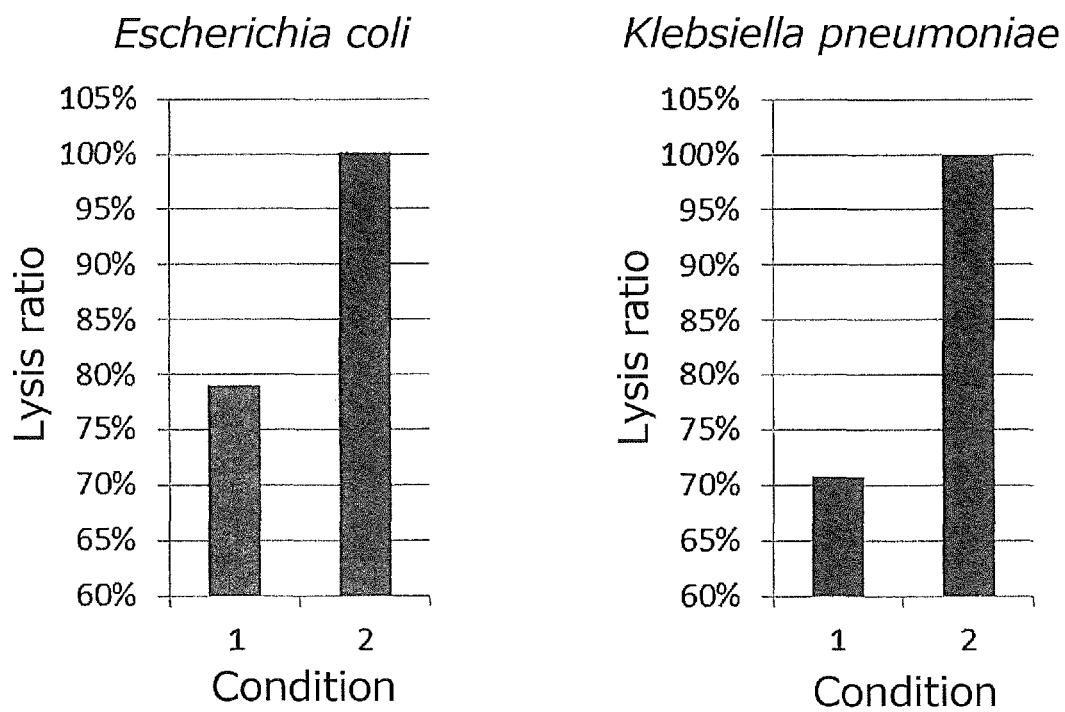

[Fig. 3]
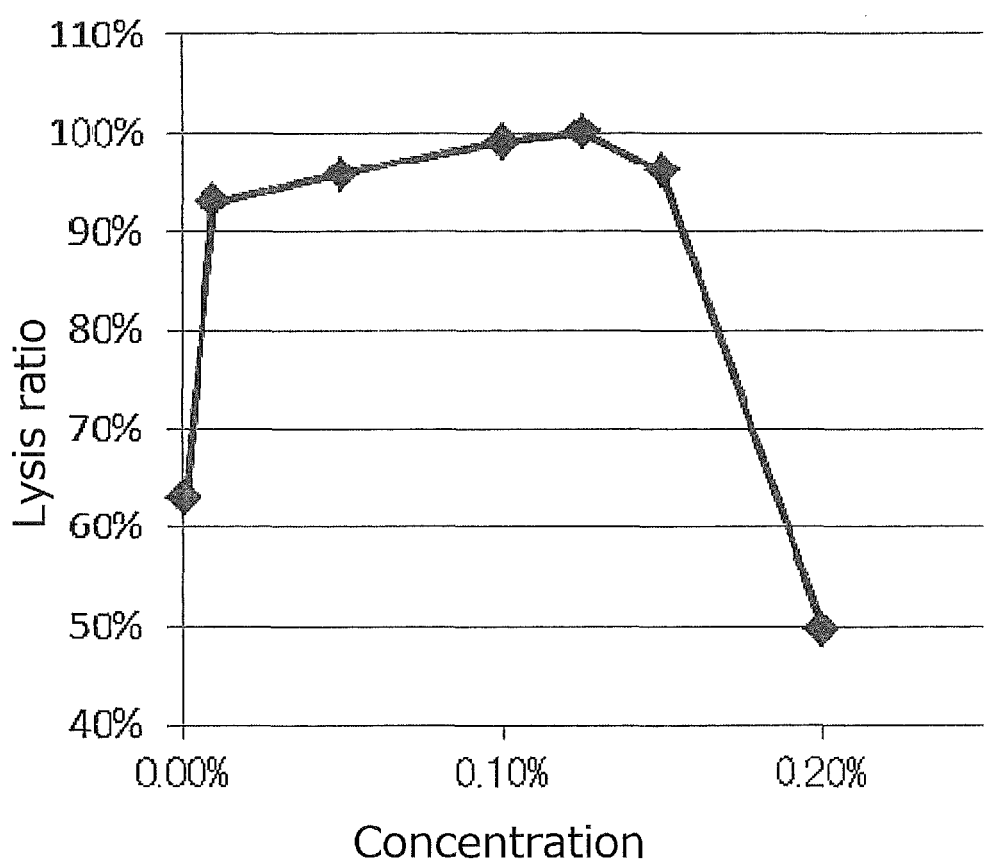

METHOD FOR DETECTING COLIFORM BACTERIA CONTAINED IN MILK

TECHNICAL FIELD

The present invention relates to a lysis method and detection method for detecting coliform bacteria, which are causative bacteria of mastitis, in milk of livestock.

BACKGROUND ART

Milk of livestock animals, of which typical examples are cow, sheep, and goat, may not be sterile, and may be contaminated with certain microorganisms due to diseases or environment. In particular, it is known that animals with a disease caused by infection of a microorganism in the udder often discharge a lot of the microorganisms into milk. Typical diseases of livestock animals caused by infection of a microorganism include mastitis.

Mastitis is inflammation of the laticifer system or milk gland tissue, and it is caused largely by invasion, colonization, and proliferation of a microorganism in the udder. Although many kinds of animals contract mastitis, it is said that, especially concerning cow's mastitis in dairy cows, 15 to 40% of the whole dairy cows contract mastitis, and thus it is one of the extremely important diseases for dairy farmers. If a dairy cow contracts mastitis, not only the milk synthesis function is inhibited to result in reduction of lactation amount, or even stop of lactation as the case may be, but also enormous economical losses are imposed on dairy farmers, such as cost of medical treatment and penalty concerning milk price due to degradation of milk quality. Furthermore, it also increases the labor of dairy farmers, since, for example, milking of teats suffering from mastitis must be separately performed for preventing infection.

Mastitis is caused by infection of various microorganisms. Among the causative bacteria, coliform bacteria, of which typical examples are *Escherichia coli* and *klebsiella*, cause systemic symptoms such as pyrexia, and local symptoms such as feeling of heat, swelling, and induration of the udder.

As the method for detecting coliform bacteria in milk, cultivation-based methods are widely used. Since the cultivation-based methods require several days for obtaining a result, they are not suitable for quick identification of causative bacteria. In contrast, identification methods based on an antigen-antibody reaction using an antibody directed to an ingredient specific to a causative bacterium, especially the immunochromatographic method, can provide the result in several tens of minutes, and therefore they are widely used in homes, consultation rooms, etc. as quick and convenient inspection methods (for example, Patent document 1). The inventors of the present invention have examined use of an immunochromatographic method also as a method for detecting a substance contained in milk of livestock animals (Patent document 2).

As for the detection of bacteria based on an antigen-antibody reaction, when an ingredient contained in bacterial cells is a target of the detection, there have also been examined methods of lysing bacterial cells, and detecting an ingredient thereof. For example, there is disclosed a method for measuring microbial cell count by allowing an enzyme of a microorganism to act on a non-fluorescent substance to generate a fluorescent substance, and measuring this fluorescent substance, wherein an agent for lysing cell membranes of the microorganism alone, or lysozyme and the cell membrane-lysing agent are added (Patent document 3).

Further, as a method for detecting multiple kinds of microorganisms, there is known a method of using a treatment with a lytic enzyme and/or a bacteriocin having a bacteriolytic activity, a surfactant, and a protein denaturant (Patent document 4). Patent document 3 describes use of a supernatant obtained by centrifugation of a homogenized food sample. Patent document 4 describes use of cultured cell suspension, but does not describe that lysis effects can be obtained in a high protein and high fat content solution such as milk.

PRIOR ART REFERENCES

Patent Documents

Patent document 1: Japanese Patent Unexamined Publication (KOKAI) No. 1-244370
Patent document 2: Japanese Patent Unexamined Publication (KOKAI) No. 2012-122921
Patent document 3: Japanese Patent Unexamined Publication (KOKAI) No. 63-167799
Patent document 4: International Patent Publication WO2005/064016 (Japanese Patent No. 4621919)
Patent document 5: Japanese Patent Unexamined Publication (KOKAI) No. 7-196463

Non-Patent Documents

Non-patent document 1: Comp. Immun. Microbiol. Infect. Dis., Vol. 6, No. 3, pp. 235-245, 1983

SUMMARY OF THE INVENTION

Object to be Achieved by the Invention

Mastitis is caused by infection of various microorganisms, and therefore antibiotics that exhibit efficacy against mastitis may differ depending on type of causative microorganism. Further, when mastitis is caused by certain specific types of bacteria, they may transmit to other teats of the individual, or other individuals, and therefore it is extremely important to quickly, conveniently, and highly sensitively identify the causative bacteria existing in milk. Especially as for coliform bacteria, which show higher proliferation rate compared with gram-positive bacteria, hence easily develop severer infection, cause very acute mastitis, and often invite even death, it is extremely important to find them, and performs treatment in an early stage of infection for preventing damage of mastitis.

The cultivation-based methods widely used as methods for detecting a bacterium have a problem that they require several days to obtain a result. In contrast, the immunological measurement methods based on an antigen-antibody reaction, such as the immunochromatographic method, have an advantage that they enable quicker and more convenient detection of causative bacteria compared with the cultivation-based methods.

In order to highly sensitively detect a specific substance contained in cells of a causative bacterium by an immunological measurement method, it is necessary to highly efficiently lyse the cells to release antigens in the inside of the cells to the outside of the cells. However, it has been revealed that when milk is used as a test sample, conventional techniques cannot provide sufficient lysis, because of the influences of proteins such as casein, milk fat globules, and so forth contained in milk in large amounts. Therefore, there has been desired a method for highly efficiently lysing coliform bacteria in milk for highly sensitive detection of causative bacteria of mastitis. However, any effective lysis method for detecting coliform bacteria contained in milk is not known.

An object of the present invention is to provide a lysis method, lysis treatment solution, detection method using an immunochromatographic device, and detection kit comprising an immunochromatographic device for detecting whether causative bacteria of mastitis are coliform bacteria or not by using milk of a livestock animal.

Means for Achieving the Object

The inventors of the present invention considered that, in order to highly sensitively detect coliform bacteria in milk, which has high protein and fat contents, and shows individual difference, it is necessary to highly efficiently extract target antigens contained in cells, and found that by simultaneously using a lytic enzyme and a plurality of kinds of surfactants for highly efficiently lysing coliform bacteria contained in milk, lysis efficiency is improved, and coliform bacteria contained in milk can be highly sensitively detected. In particular, it is known that if lysozyme is used as the lytic enzyme in combination with an anionic surfactant, especially sodium laurylsulfate (sodium dodecylsulfate), lysozyme loses the enzymatic activity thereof (Patent document 5 mentioned above). However, as a result of the investigations of the inventors of the present invention, it was found that if an anionic surfactant is used at a concentration within an appropriate range, the lysis ratio is markedly improved on the contrary, and coliform bacteria contained in milk can be highly sensitively detected, and they accomplished the present invention.

The present invention thus provides the followings.

[1] A method for lysing coliform bacteria, which comprises the step of mixing milk obtained form a large livestock animal with a lysis agent containing a lytic enzyme and at least one kind of anionic surfactant to lyse coliform bacteria existing in the milk.

[2] The method according to [1], wherein the lytic enzyme is lysozyme.

[3] The method according to [1] or [2], wherein the milk and the lysis agent are mixed so that final concentration of the anionic surfactant becomes 0.01 to 0.15%.

[4] The method according to any one of [1] to [3], wherein the lysis agent further contains at least one kind of nonionic surfactant.

[5] The method according to [4], wherein the anionic surfactant comprises an alkyl sulfate.

[6] The method according to any one of [1] to [5], wherein the nonionic surfactant comprises a polyoxyethylene alkyl phenyl ether.

[7] A lysis agent for use in lysis of coliform bacteria contained in milk of a livestock animal, which contains a lytic enzyme and at least one kind of anionic surfactant.

[8] The lysis agent according to [7], which is for use in a method for diagnosing mastitis of a livestock animal.

[9] The lysis agent according to [7] or [8], wherein the anionic surfactant is contained at such a concentration that final concentration thereof becomes 0.01 to 0.15% when the milk and the lysis agent are mixed.

[10] A method for detecting coliform bacteria contained in milk of a livestock animal, which comprises the method according to any one of [1] to [6], and further comprises the step of detecting a specific substance derived from the inside of the cells of coliform bacteria and released by lysis.

[11] The method according to [10], wherein the step of detecting a specific substance is performed by an immunochromatographic method.

[12] The method according to [11], wherein the immunochromatographic method comprises: (1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) the step of flowing the milk up to the second part or a part existing downstream therefrom to obtain a detectable signal of the label at the second part or a part existing downstream therefrom.

[13] The method according to [12], wherein the labeled first antibody directed to the specific substance is retained in the first part.

[14] The method according to [12] or [13], wherein the third part is constituted by two or more kinds of members having voids that can remove milk fat globules of different particle sizes, respectively.

[15] The method according to [14], wherein the third part is constituted by a first member disposed downstream and a second member disposed upstream, and retention particle size of the second member is larger than retention particle size of the first member.

[16] A kit for detecting coliform bacteria contained in milk of a livestock animal, which comprises the lysis agent according to any one of [7] to [9], and an immunochromatographic device for detecting a specific substance contained in milk, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk.

The present invention also provides the followings.

[1] A method for lysing coliform bacteria contained in milk, which comprises the step of mixing a lysis agent containing lysozyme, an ionic surfactant, and a nonionic surfactant with the milk to lyse coliform bacteria existing in the milk.

[2] The lysis method according to [1], wherein the ionic surfactant is an anionic surfactant.

[3] The lysis method according to [2], wherein the anionic surfactant comprises an alkyl sulfate; and/or the nonionic surfactant comprises a polyoxyethylene alkyl phenyl ether.

[4] The lysis method according to [2] or [3], wherein, in the step of mixing the lysis agent with the milk to lyse the bacteria existing in the milk, final concentration of the anionic surfactant is not lower than 0.01% and not higher than 0.15%.

[5] The lysis method according to [4], wherein, in the step of mixing the lysis agent with the milk to lyse the bacteria existing in the milk, final concentration of lysozyme is not lower than 0.1 mg/ml and not higher than 200 mg/ml; and/or in the step of mixing the lysis agent with the milk to lyse the bacteria existing in the milk, final concentration of the nonionic surfactant is not lower than 0.03% and not higher than 10%.

[6] A method for detecting coliform bacteria contained in milk, which comprises:
the step of mixing the lysis agent with the milk to lyse coliform bacteria existing in the milk defined in any one of [1] to [5], and further comprises:
the step of detecting a specific substance derived from the inside of the bacterial cells and released by lysis.

[7] The detection method according to [6], which is performed by an immunochromatographic method.

[8] The method according to [7], wherein the immunochromatographic method comprises:
(1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) the step of flowing the milk up to the second part or a part existing downstream therefrom to obtain a detectable signal of the label at the second part or a part existing downstream therefrom.

[9] The method according to [8], wherein the labeled first antibody directed to the specific substance is retained in the first part.

[10] The method according to [8] or [9], wherein the third part is constituted by two or more kinds of members having voids that can remove milk fat globules of different particle sizes, respectively.

[11] The method according to [10], wherein the third part is constituted by a first member disposed downstream and a second member disposed upstream, and retention particle size of the second member is larger than retention particle size of the first member.

[12] The lysis agent defined in any one of [1] to [5].

[13] The lysis agent according to [12], which is for use in a method of diagnosing mastitis of a livestock animal.

[14] A kit for detecting coliform bacteria contained in milk, which comprises: the lysis agent according to [12] or [13], and an immunochromatographic device for detecting a specific substance contained in milk, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk.

Effect of the Invention

According to the present invention, coliform bacteria contained in milk can be quickly, conveniently, and highly sensitively detected on the spot. In particular, in the case of diagnosis of cow's mastitis, if a visually recognizable label is used, the diagnosis can be performed in a dairy farm without using any apparatus etc., so that a causative bacterium can be quickly specified before further aggravation of pathological conditions, and appropriate treatment policies such as selection of a suitable antibiotics, and countermeasures for preventing expansion of infection can be determined at an early stage.

BRIEF DESCRIPTION OF THE DRAWINGS

FIG. 1 shows a schematic sectional view of the test strip of the immunochromatographic device used in Example 2, which comprises a labeled antibody-impregnated member 1 (first part), a membrane carrier 2 for chromatographic development (second part), a part 3 for capturing, a member 4 serving as both a member for sample addition and a member for removal of fat globules (third part), a member 5 for absorption, a substrate 6, and a member 7 for removal of fat globules (third part).

FIG. 2 shows effect of sodium dodecylsulfate (SDS) in the presence of lysozyme and a nonionic surfactant in detection of *Escherichia coli* by an immunochromatographic method.

FIG. 3 shows effect of sodium dodecylsulfate (SDS) in the presence of a lytic enzyme and a nonionic surfactant in detection of *Escherichia coli* by an immunochromatographic method.

MODES FOR CARRYING OUT THE INVENTION

Hereafter, the present invention will be explained in more detail. In the present invention, when a numerical value range is represented as "X to Y", the range includes the values X and Y as the minimum and maximum values. The symbol "%" is used for indicating percent on mass basis, unless especially indicated. The expression "A and/or B" means at least one of A and B, including the cases of referring to only A, only B, and A and B.

The present invention provides a lysis agent for lysing coliform bacteria contained in milk. The lysis agent of the present invention contains a lytic enzyme and a specific surfactant.

[Lytic Enzyme]

Type of the lytic enzyme used in the present invention is not particularly limited, and arbitrary two or more kinds of lytic enzymes may also be used in combination, as required. As for the causative bacterium of mastitis, infection by *Escherichia coli*, *Klebsiella bacterium*, or *Staphylococcus aureus* frequently occurs, and therefore it is also preferable to use one or two or more kinds of lytic enzymes that can exhibit bacteriolytic action to these microorganisms in combination. For example, one or two or more kinds of lytic enzymes selected from lysozyme, lysostaphin, pepsin, glucosidase, galactosidase, achromopeptidase, β-N-acetylglucosaminidase, and so forth can be used.

When presence of coliform bacteria is especially suspected as the causative bacteria of mastitis, it may be preferable to use a lytic enzyme that specifically exhibits a bacteriolytic action against coliform bacteria, alone or in combination with another lytic enzyme. For example, there has been proposed a method of using lysozyme as a lytic enzyme and a cell membrane lysing agent (Japanese Patent Unexamined Publication (KOKAI) No. 63-167799).

Lysozyme is a protein consisting of a single peptide of 14.6 kDa, and can lyse cells of bacteria by cleaving the β(1-4) glycosidic linkage between N-acetylmuramic acid and N-acetylglucosamine in the peptidoglycan layer. Lysozyme can be obtained by purchasing a marketed product.

Content of the lytic enzyme in the lysis agent (when two or more kinds of lytic enzymes are used, it is the content as the total amount of the lytic enzymes) is not particularly limited so long as a lysis ratio effective for the detection is secured. However, the content can be determined so that the final concentration of the lytic enzyme in the mixture with milk becomes 0.1 mg/ml or higher, preferably 0.2 mg/ml or higher, more preferably 0.5 mg/ml or higher, further preferably 1.0 mg/ml or higher, particularly preferably 2.0 mg/ml or higher, in terms of lysozyme. As for the upper limit of the content of the lytic enzyme, the content can be determined as required from the economical point of view, or the like, and irrespective of how the lower limit is defined, it can be 200 mg/ml or lower, preferably 100 mg/ml or lower, more preferably 75 mg/ml or lower, further preferably 50 mg/ml or lower, particularly preferably 25 mg/ml or lower.

[Surfactant]

A surfactant that ionizes and becomes an ion, when it is dissolved in water, is referred to as ionic surfactant, and a surfactant that does not become an ion is referred to as non-ionic (nonionic) surfactant. Ionic surfactant is further classified into anionic surfactant, cationic surfactant, and ampholytic surfactant.

In the present invention, together with the lytic enzyme, at least one kind of ampholytic surfactant, at least one kind of anionic surfactant, or at least one kind of cationic surfactant, or a combination of any of these is used. It is preferable to use, together with the lytic enzyme, at least one kind of nonionic surfactant, or at least one kind of anionic surfactant, or a combination of these. It is more preferable to use, together with the lytic enzyme, at least one kind of nonionic surfactant, and at least one kind of anionic surfactant in combination.

Types of surfactants to be used are not particularly limited. As the nonionic surfactant, any of those of ester ether type, ester type, and ether type can be preferably used. More specifically, examples include polyoxyethylene alkyl ethers, polyoxyethylene alkyl phenyl ethers, fatty acid sorbitan esters, alkyl polyglucosides, fatty acid diethanolamides, alkyl monoglyceryl ethers, and so forth. Especially preferred examples include polyoxyethylene alkyl phenyl ethers, more specifically polyoxyethylene (10) octyl phenyl ether, and so forth. It has been confirmed that polyoxyethylene alkyl phenyl ethers such as polyoxyethylene (10) octyl phenyl ether can be effectively used also in the immunochromatographic method.

Content of the nonionic surfactant in the lysis agent (when two or more kinds of nonionic surfactants are used, it is the content as the total amount of the nonionic surfactants) is not particularly limited so long as, for example, when an immunochromatographic method is used, flow of a developing solution is secured. However, in any case, as for the lower limit thereof, the content can be determined so that the final concentration of the nonionic surfactant in the mixture with milk becomes 0.03% or higher, preferably 0.05% or higher, more preferably 0.075% or higher, further preferably 0.1% or higher, particularly preferably 0.3% or higher. As for the upper limit of the content of the nonionic surfactant, the content can be determined so that the reaction catalyzed by the lytic enzyme and antigen-antibody reactions are not significantly inhibited, and in any case, it can be 10% or lower, preferably 7.5% or lower, more preferably 5% or lower, still more preferably 3% or lower, particularly preferably 2% or lower.

Examples of the anionic surfactant include sodium alkylsulfates such as sodium dodecylsulfate and sodium myristylsulfate, sodium N-acylsarcosinates such as sodium N-lauroylsarcosinate and sodium N-myristoylsarcosinate, sodium dodecylbenzenesulfonate, hydrogenated coconut fatty acid monoglyceride monosodium sulfate, sodium laurylsulfoacetate, N-acylglutamates such as sodium N-palmitoylglutamate, N-methyl-N-acylalanine sodium, and sodium α-olefinsulfonates, and so forth, but the anionic surfactant is not particularly limited.

Content of the anionic surfactant in the lysis agent (when two or more kinds of anionic surfactants are used, it is the content as the total amount of the anionic surfactants) is not particularly limited, so long as a lysis ratio effective for the detection is secured. However, as for the lower limit thereof, the content can be determined so that the final concentration thereof in the mixture with milk becomes 0.0001% or higher, preferably 0.0002% or higher, more preferably 0.0005% or higher, further preferably 0.001% or higher, still further preferably 0.005% or higher, particularly preferably 0.01% or higher, irrespective of the content of the lytic enzyme. As for the upper limit of the content of the anionic surfactant, the content can be determined so that the reaction catalyzed by the lytic enzyme and antigen-antibody reactions are not significantly inhibited. In any case, it can be 1% or lower, preferably 0.75% or lower, more preferably 0.5% or lower, further preferably 0.3% or lower, still further preferably 0.2% or lower, particularly preferably 0.15% or lower.

Examples of the ampholytic surfactant include those of amino acid type (alkylaminofatty acid salts), betaine type (alkyl betaines), amine oxide type (alkylamine oxides), and so forth, but it is not particularly limited. More specific examples include dimethylammoniopropanesulfonates, dodecyldimethylammoniobutyrates, lauryl betaine, and amidopropyl betaine. Further specific examples include n-tetradecyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate, and N-dodecyl-N,N-(dimethylammonio)butyrate.

As the cationic surfactant, any of those of amine salt type and quaternary ammonium salt type can be preferably used. More specific examples include distearyldimethylbenzylammonium chloride, benzalkonium chloride, hexadecyltrimethylammonium bromide, hexadecyltrimethylammonium bromide, myristyltrimethylammonium bromide, and so forth.

[Example of Composition]

In one of the most preferred embodiments, the lysis agent comprises lysozyme, an anionic surfactant, and a nonionic surfactant. For the lysis agent containing lysozyme, an anionic surfactant, and a nonionic surfactant, preferred examples of the nonionic surfactant include polyoxyethylene alkyl phenyl ethers. Concentrations of such ingredients of the lysis agent can be determined so that, in the step of lysing bacteria existing in milk by mixing the lysis agent with the milk, the final concentration of lysozyme is not lower than 0.1 mg/ml and not higher than 200 mg/ml, the final concentration of the anionic surfactant is not lower than 0.01% and not higher than 0.15%, and the final concentration of the nonionic surfactant is not lower than 0.03% and not higher than 10%.

[Other Ingredients]

The lysis agent of the present invention may contain, besides the lytic enzyme and the surfactant, one or more kinds of other ingredients, so long as the intended effect is not markedly degraded. Preferred examples of the ingredients other than the lytic enzyme and the surfactant include a substance that has an effect of promoting the lysis. Specific examples include glutaraldehyde, halogen compounds, chlorhexidine, alcohols (for example, methanol, ethanol, 1-propanol, 2-propanol, 1-butanol, 2-butanol, 2-methyl-1-propanol, 2-methyl-2-propanol), phenol, hydrogen peroxide, acrinol, guanidine and salt thereof, chelating agents, organic acids and salts thereof, polyhydric alcohols (for example, ethylene glycol, propylene glycol, diethylene glycol, and glycerin), and reducing agents such as 2-mercaptoethanol, dithiothreitol, cystine, and thiophenol, but they are not limited to these.

[Lysis Conditions and Lysis Ratio]

In the present invention, the lysis agent can be used by mixing it with milk. Mixing ratio of milk and the lysis agent is not particularly limited, so long as the final concentrations of the lytic enzyme etc. are properly maintained, and sufficient lysis ratio can be secured. If the lysis agent is used in a volume relatively small with respect to milk, the milk is not diluted. Therefore, it can be expected that cells can be detected with higher sensitivity. When the lysis agent is used in a volume relatively large with respect to milk, influences of fat globules and proteins contained in milk are reduced, and therefore it can be expected that cells can be detected in a shorter time. From the viewpoint that a higher ratio of milk in the mixture of milk and the lysis agent (milk/(milk+lysis agent)×100) can provide higher detection sensitivity, the ratio can be, for example, 5% or higher, preferably 10% or higher, more preferably 20% or higher, further preferably 30% or higher, irrespective of the other conditions. As for the upper limit of the ratio, if the lysis agent solidified by drying or the like is used, the ratio of milk can be made to be 100%, irrespective of the other conditions. The ratio of the milk can be 90% or lower, 80% or lower, 70% or lower, 60% or lower, or 50% or lower, irrespective of the other conditions. As for the upper limit, the ratio may be determined in consideration of ease of mixing, stability of the lysis agent as a solution, and so forth.

In the present invention, it is sufficient to simply mix milk with the lysis agent. Temperature at the time of mixing, and treatment time for allowing the enzyme to act following the mixing are not particularly limited, so long as the lytic enzyme used can exhibit the activity, and the temperature may usually be room temperature. The treatment time for allowing the reaction after the mixing can be appropriately determined by those skilled in the art in consideration of lysis ratio. In the present invention, since combination and concentrations of lytic enzyme and surfactant appropriate for coliform bacteria are used, the treatment time can be markedly shortened compared with a case where only a lytic enzyme is used. In the present invention, the treatment time is generally about several tens of minutes to several hours, and more specifically, it can be 120 minutes or shorter, preferably 60 minutes or shorter, more preferably 45 minutes or shorter, further preferably 25 minutes or shorter, still further preferably 20 minutes or shorter, still more further preferably 15 minutes or shorter. The treatment time can also be made to be substantially 0 (after milk and the lysis agent are mixed, the mixture is immediately subjected to the measurement). According to the present invention, even by the treatment for such a short time, a lysis ratio of 90% or higher is secured, and coliform bacteria can be detected with high sensitivity.

According to the investigations of the inventors of the present invention, it could be confirmed that, with the conditions described in the examples of this specification, a lysis ratio of 100% can be attained by treating milk containing about $1 \times 10^5$ cells/ml of *Escherichia coli* with the lysis agent of the present invention for about 10 minutes. As for the basis of the lysis ratio, lysis ratio observed for a suspension of a target bacteria subjected to a preliminary treatment with a nonionic surfactant of a proper concentration, and then further subjected to ultrasonication, and a sufficient enzyme treatment, as required, can be defined as 100%.

[Detection Means]

Coliform bacteria lysed according to the present invention can be detected by various kinds of immunological methods using an ingredient of bacterial cells as an antigen. Examples of immunological measurement method include, for example, immunochromatographic method, agglutination reaction method, enzyme immunoassay (ELISA), radioimmunoassay (RIA), fluoroimmunoassay (FIA), and so forth, but it is not limited to these.

At the time of performing the immunological methods, a substance for blocking for preventing non-specific adsorption, or a substance for preventing cross-reaction with bacteria other than the target bacterium may be used. In particular, in order to prevent reaction of the antibody used and the protein A of *Staphylococcus aureus,* globulin that does not participate in the reaction with the antigen can be added. When globulin is used, it can be added in an amount of 0.01 μg/ml or larger, preferably 0.1 μg/ml or larger, more preferably 1 μg/ml or larger, as the final concentration at the time of the reaction, from the viewpoint of suppressing false positive results. Further, in any case, from the viewpoint of not inhibiting the objective antigen-antibody reaction, it can be used in an amount of 10 mg/ml or smaller, preferably 5 mg/ml or smaller, more preferably 1 mg/ml or smaller. Such conditions concerning the final concentration are especially suitable for the immunochromatographic method.

When an immunochromatographic method is used, it can be carried out typically as follows.

[Immunochromatographic Method and Immunochromatographic Device]

An antigen-antibody reaction can be detected by the sandwich assay using a "labeled first antibody directed to a specific substance" retained by a first part, and a "second antibody directed to the specific substance" immobilized on a second part. Alternatively, an antigen-antibody reaction may also be detected by the competition method using a labeled specific substance retained by a first part, and an antibody directed to the specific substance immobilized on a second part. However, in the present invention, the sandwich assay method is preferred, since it shows high detection sensitivity and gives a line indicating detection of antibody as a positive result.

The immunochromatographic device is a device for detecting a specific substance contained in milk by an immunochromatographic method, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk. As a specific example of the structure of the test strip, that of the test strip of which schematic sectional view is shown in FIG. 2 can be mentioned. In FIG. 2, a member 7 for removal of fat globules (third part) is disposed downstream from a member 4 for sample addition, and upstream from a labeled antibody-impregnated member (first part) 1.

The immunochromatographic device can be produced in a known manner by using marketed materials.

The material used for the first part is not particularly limited, so long as a material enabling immunochromatography is chosen, but preferred examples include a fiber matrix of cellulose derivative etc., filter paper, glass fiber, cloth, cotton, and so forth.

The material used for the second part is not particularly limited, so long as a material enabling immunochromatography is chosen, but preferred examples include cellulose nitrate, mixed cellulose nitrate ester, polyvinylidene fluoride, nylon, and so forth.

The material used for the third part preferably has voids that enable removal of milk fat globules contained in milk and having a diameter of about 1 to ten and several micrometers. The third part must be disposed upstream from the aforementioned second part consisting of a porous membrane having a pore diameter of several tens to several hundreds nm, and is preferably disposed upstream from the aforementioned first part, i.e., at a position at which a sample solution first contacts with and passes through the test strip.

The voids of the third part may have a size that enables removal of milk fat globules, and retention particle size is preferably 0.1 to 10 µm, more preferably 1 to 3.5 µm. The material is not particularly limited, so long as a material having voids showing a retention particle size within the aforementioned range is chosen, but preferred examples include a matrix of fibers such as cellulose derivatives, filter paper, glass fiber, cloth, cotton, and so forth. The retention particle size means such a particle size of milk fat globules that milk fat globules having a particle size not smaller than the retention particle size cannot pass through the voids and retained by the third part, and substantially corresponds to average pore size of the voids of the third part, and 50% or more, preferably 60% or more, more preferably 70% or more, still more preferably 80% or more, particularly preferably 90% or more, most preferably 98% or more, of milk fat globules having a particle size not smaller than the retention particle size cannot pass through the voids and are retained by the third part. Ratio of milk fat globules to be retained can be measured by a method well known to those skilled in the art. For example, the catalogue of GF/B provided by GE Healthcare Bioscience describes that the retention particle size (particle diameter for which retention efficiency is 98%, the term retention particle size used in this specification has this meaning, unless especially indicated) thereof is 1.0 µm, and such a particle size as mentioned above can be confirmed by a method well known to those skilled in the art.

The aforementioned third part may consist of a single kind of material having a specific retention particle size, or may consist of a laminate comprising materials having different retention particle sizes and integrally adhered so that the retention particle size becomes smaller stepwise, in order to increase milk fat globule separation efficiency. Such a third part as mentioned above constituted by two or more kinds of members that can remove milk fat globules of different particle sizes constitutes a preferred embodiment of the present invention, and in a more preferred embodiment of the present invention, the third part is constituted with a first member disposed downstream and a second member disposed upstream, and the retention particle size of the second member is larger than the retention particle size of the first member. When the third part is constituted with such two kinds of members, it is preferred that the retention particle size of the first member disposed downstream is 1.0 to 2.0 µm, and the retention particle size of the second member disposed upstream is 3.0 to 3.5 µm. In order to highly sensitively detect a specific substance from milk containing milk fat globules of high concentration and wide particle size distribution, especially such milk not diluted after milking, it is preferred that the third part is constituted with a combination of a member having a small retention particle size and a member having a large retention particle size.

The aforementioned first part retains a labeled first antibody directed to a specific substance, or a labeled specific substance. If the first part retains a labeled first antibody directed to a specific substance, the specific substance can be detected by the sandwich assay method. If the first part retains a labeled specific substance, the specific substance can be detected by the competition method. Since the sandwich assay method that shows high detection sensitivity and gives a line indicating detection of antibody as a positive result is more preferred for the present invention, the first part preferably retains a labeled first antibody directed to a specific substance.

When the first part is made to retain a labeled first antibody directed to a specific substance, two kinds of antibodies, the first antibody directed to the specific substance, and a second antibody also directed to the specific substance, are used. In order to enable detection of the specific substance by the sandwich assay method, the aforementioned first antibody and second antibody are antibodies that can simultaneously bind to the specific substance, and it is preferred that the epitope of the specific substance to be recognized by the aforementioned first antibody is different from the epitope of the specific substance to be recognized by the aforementioned second antibody.

In the present invention, in order to obtain a detectable signal, the first antibody or the specific substance retained by the first part is labeled. Examples of the label used for the present invention include a colored particle, enzyme, radioisotope, and so forth, and it is preferable to use a colored particle that can be visually detected without any special equipment. Examples of the colored particle include metal microparticles such as those of gold and platinum, nonmetallic particles, latex particles, and so forth, but are not limited to these. The colored particle may have any size so long as the colored particle has such a size that it can be transported downstream through the inside of the voids of the test strip, but it preferably has a size of 1 nm to 10 µm, more preferably 5 nm to 1 µm, still more preferably 10 nm to 100 nm, in diameter.

[Object of Detection]

According to the present invention, coliform bacteria contained in milk can be detected. The term "coliform bacteria" used in the present invention refers to bacteria including *Escherichia coli*, *Klebsiella* bacteria, *Citrobacter* bacteria, *Enterobacter* bacteria, and *Proteus* bacteria, unless especially indicated. *Klebsiella* bacteria include *Klebsiella pneumoniae* and *Klebsiella oxytoca*. According to the present invention, coliform bacteria contained in milk obtained from a livestock animal such as cow as it is, which contains fat globules and proteins of high concentration, can be detected by using the lysis agent containing appropriately formulated lytic enzyme and surfactant.

The specific substance measured in the present invention may be any substance so long as it is a substance that can be measured by the immunochromatographic method, but it is preferably a component of a bacterium or a substance that is secreted by a bacterium. The specific substance is more preferably the L7/L12 ribosomal protein of a bacterium. High detection sensitivity can be obtained for the L7/L12 ribosomal protein, since it exists in cells in a large copy number. As described in the examples mentioned later, an antibody that can recognize a particular bacterium that causes mastitis with distinguishing it from other bacteria at species or genus level can actually be obtained by the known method described below. Types of the bacteria are not particularly limited, and they may be gram-positive bacteria, or gram-negative bacteria. Examples include, for example, gram-positive bacteria such as staphylococci (bacteria belonging to the genus *Staphylococcus*), preferably *Staphylococcus aureus*, *Escherichia coli*, bacteria belonging to the genus *Klebsiella*, and so forth, but the bacteria are not limited to these.

[Antibody]

The aforementioned antibody can be prepared by the method described in International Patent Publication WO00/06603. When the bacterial ribosomal protein L7/L12 is used as the antigen, the antibody can be prepared by using a full length protein or a partial peptide of the bacterial ribosomal protein L7/L12 as an antigen, but it is preferably prepared by using the full length protein as an antigen. An antiserum containing an antibody (polyclonal antibody) that recognizes the L7/L12 ribosomal protein can be obtained by inoculating such a partial peptide or full length protein as mentioned above as it is or crosslinked with a carrier protein to an animal, together with an adjuvant as required, and collecting the serum of the animal. Further, the antibody purified from the antiserum can also be used. Examples of the animal used for the inoculation include sheep, horse, goat, rabbit, mouse, rat, and so forth, and sheep, rabbit, and so forth are especially preferred for preparing polyclonal antibodies. Further, it is more preferable to use, as the antibody, a monoclonal antibody obtained by a known method in which a hybridoma cell is prepared, and in such a case, mouse is preferred as the animal. If, as such a monoclonal antibody, a monoclonal antibody that reacts with the ribosomal protein L7/L12 of a specific bacterium that causes mastitis, but does not react with the ribosomal protein L7/L12 of a bacterium that causes mastitis other than the above specific bacterium is retrieved by screening, it can be utilized for diagnosing whether an animal suffers from infection by the bacterium or not.

A monoclonal antibody that recognizes a substance other than the ribosomal protein L7/L12 as an antigen may also be used, so long as the antibody is a monoclonal antibody that reacts with a component of a specific bacterium that causes mastitis or a substance secreted by such a bacterium, but does not react with a component of a bacterium that causes mastitis other than the foregoing specific bacterium or a substance secreted by such a bacterium.

Further, as the monoclonal antibody, it is preferable to use a monoclonal antibody of which antigen-antibody reaction is not inhibited by any contaminants other than the specific substance contained in milk. For example, milk contains a large amount of proteins such as casein, and they may inhibit the reaction of the specific substance and the monoclonal antibody. When a monoclonal antibody directed to the specific substance is prepared in a conventional manner, for example, a monoclonal antibody of which antigen-antibody reaction is not inhibited by casein or the like, or a monoclonal antibody of which antigen-antibody reaction is hardly affected by casein or the like may be preferably chosen and used. Such a monoclonal antibody can be easily obtained by preparing monoclonal antibodies that specifically react with an antigen in a usual manner, and then selecting a monoclonal antibody of which antigen-antibody reaction is not substantially inhibited by a contaminant such as casein by examining whether the antigen-antibody reaction is inhibited or not in the presence of the contaminant.

[Others]

In the present invention, the test strip described above may be used as it is as an immunochromatographic device, or the test strip may be stored in a case to constitute an immunochromatographic device. In the former case, if a large volume of milk is used as a sample, the immunochromatographic device is preferably used by directly immersing one end of the test strip into the sample contained in a container. In the latter case, if the volume of milk as a sample is small, the immunochromatographic device is preferably used by measuring a predetermined volume of the sample with a pipette or the like, and dropping the sample to the test strip. In the latter case, the case may have any shape so long as the test strip can be stored. The case may be formed with any material, and preferred examples include polypropylene, polycarbonate, and so forth.

The immunochromatographic device of the present invention can also be provided as a kit comprising a container such as microtube, and an additive solution, for example, an additive solution containing a lytic enzyme or surfactant for lysing the bacterium to elute the ribosomal protein L7/L12 into the solution.

EXAMPLES

Example 1

Effect of Sodium Dodecylsulfate (SDS) in the Presence of Lysozyme and Nonionic Surfactant in Detection of *Escherichia Coli* by Immunochromatographic Method (1) Preparation of Monoclonal Antibody Directed to Ribosomal Protein L7/L12

As the antibody to be labeled with gold colloid, *Escherichia coli* ribosomal protein L7/L12 monoclonal antibody was used. According to the method described in International Patent Publication WO00/06603, Example 5, the *Escherichia coli* L7/L12 ribosomal protein was obtained, and monoclonal antibodies were prepared by using this protein. Among the monoclonal antibodies, a combination of two kinds of monoclonal antibodies (EC-1 and EC-2) that can simultaneously bind to different sites of the L7/L12 ribosomal protein of the aforementioned bacterium or other coliform bacteria was selected.

(2) Preparation of Immunochromatographic Device

An immunochromatographic device was prepared as follows.

(a) Gold Colloid-Labeled Antibody-Impregnated Member

A gold colloid solution (particle size 60 nm, 0.9 mL, BB International) was mixed with 0.1 M potassium phosphate, pH 7.0, the monoclonal antibody EC-2 (100 µg/mL) to be labeled with gold colloid was added to the mixture, and the resulting mixture was left standing at room temperature for 10 minutes so that the antibody bound to the gold colloid particle surfaces. Then, a 10% aqueous solution of bovine serum albumin (BSA) was added at a final concentration of 1% in the gold colloid solution, so that the remaining surfaces of the gold colloid particles were blocked with BSA, to prepare a solution of the monoclonal antibody EC-2 labeled with gold colloid (henceforth referred to as "gold colloid-labeled antibody"). This solution was centrifuged (at 15000 rpm for 5 minutes) to precipitate the gold colloid-labeled antibody, and the supernatant was removed to obtain the gold colloid-labeled antibody. This gold colloid-labeled antibody was suspended in 20 mM Tris-hydrochloric acid buffer (pH 8.2) containing 0.25% BSA, 2.5% sucrose, and 35 mM NaCl to obtain a gold colloid-labeled antibody solution. A glass fiber pad of a strip-like shape (10 mm×300 mm) was impregnated with the gold colloid-labeled antibody solution (2 mL), and dried at room temperature under reduced pressure to obtain a gold colloid-labeled antibody-impregnated member 1 (first part).

(b) Part for Capturing Complex of Antigen and Gold Colloid-Labeled Antibody

A nitrocellulose membrane having a width of 25 mm and a length of 300 mm was prepared as a membrane carrier 2 for chromatographic development with chromatography medium (second part).

A solution containing the monoclonal antibody EC-1 (1.5 mg/mL) was applied in the shape of a line in a volume of 1 μL/cm to the membrane carrier 2 for chromatographic development at a position of 10 mm from the end on the side of the chromatography development starting point, and dried at 50° C. for 30 minutes, and then the membrane carrier was immersed in a 0.5% sucrose solution for 30 minutes, and dried overnight at room temperature to obtain a part 3 for capturing the complex of the *Escherichia coli* ribosomal protein L7/L12 antigen and the gold colloid-labeled antibody.

(c) Preparation of Immunochromatographic Device

A sectional view of immunochromatographic device is shown in FIG. 1. In addition to the aforementioned labeled antibody-impregnated member 1 and membrane carrier 2 for chromatographic development, 25 mm GF/DVA (filter member 4 having a thickness of 776 μm and consisting of glass fibers, retention particle size 3.5 μm, GE Healthcare Bioscience) and 20 mm GF/AVA (filter member 7 having a thickness of 299 μm and consisting of glass fibers, retention particle size 1.7 μm, GE Healthcare Bioscience) were adhered to each other as a member serving as both the member for sample addition and the member for removal of fat globules (third part), and filter paper as the member 5 for absorption was further prepared. After these members were adhered on a substrate 6 (thickness 254 μm, made of polystyrene, having adhesive for adhering the members), they were cut in a width of 5 mm to prepare the immunochromatographic device.

(3) Test

Measurement for cow's milk using the immunochromatographic device was performed as follows.

Milk (100 μl) containing *Escherichia coli* (ATCC 25922 strain) or *Klebsiella pneumoniae* (ATCC 13883 strain), which is a kind of species of coliform bacteria, at a final concentration of $1\times10^5$ (cfu/ml) was put into a microtube, 150 μl of a lysis treatment solution (1% (final concentration) of Triton X, 2.2 mg/ml of lysozyme (titer 0.8 mg lysozyme/mg of dry weight, Wako Pure Chemical Industries), 0.1 M MOPSO, pH 7.5) was added to the milk and mixed therein at room temperature, and the resulting mixture was left standing for 10 minutes.

As the cow's milk, marketed milk for drinking was used. The aforementioned immunochromatographic device was immersed into the above mixed solution from the member 4 for sample addition, chromatographic development was allowed by leaving the device standing at room temperature for 30 minutes, and then for determining the presence or absence of capture of the complex of the ribosomal protein L7/L12 antigen and the gold colloid-labeled antibody by the aforementioned part 3 for capturing, a reddish purple line that became more or less conspicuous in proportion to the capture amount was measured by an apparatus C10066 (Hamamatsu Photonics). The lysis ratio for each condition was calculated as a relative ratio to the lysis ratio observed in a cell suspension containing Triton X-100 at a final concentration of 1.0% that was preliminarily stiffed overnight, ultrasonicated (output 10, 1 minute×10 times), and then subjected to a lysis treatment at 37° C. for 60 minutes with 2.2 mg/ml of lysozyme, 0.1 M MOPSO, pH 7.5, which lysis ratio was taken as 100%. The results of a case where sodium dodecylsulfate (SDS) was added at a final concentration of 0.01% to the aforementioned lysis treatment solution (condition 2) and a case where sodium dodecylsulfate (SDS) was not added (condition 1) were compared.

The results are shown in FIG. 2. It was revealed that addition of sodium dodecylsulfate (SDS) markedly improved the lysis ratio.

Example 2

Effect of Sodium Dodecylsulfate (SDS) in the Presence of Lytic Enzyme and Nonionic Surfactant in Detection of *Escherichia Coli* by Immunochromatographic Method Measurement for cow's milk using the immunochromatographic device was performed as follows.

Milk (100 μl) containing *Escherichia coli* at a final concentration of $1\times10^5$ (cfu/ml) was put into a microtube, 150 μl of a lysis treatment solution (1% (final concentration) of Triton X-100, 2.2 mg/ml of lysozyme, 0.1 M MOPSO, pH 7.5) was added to the milk and mixed therein at room temperature, and the resulting mixture was left standing for 10 minutes. As the cow's milk, marketed milk for drinking was used. The aforementioned immunochromatographic device was immersed into the above mixed solution from the member 4 for sample addition, chromatographic development was carried out by leaving the device standing at room temperature for 30 minutes, and then for determining the presence or absence of capture of the complex of the ribosomal protein L7/L12 antigen and the gold colloid-labeled antibody by the aforementioned part 3 for capturing, a reddish purple line that became more or less conspicuous in proportion to the capture amount was measured by an apparatus C10066 (Hamamatsu Photonics). SDS was added to the lysis treatment solution at various concentrations, and lysis ratio for each concentration of SDS (0.01 to 0.15% as the final concentration) was calculated as a relative lysis ratio to the lysis ratio observed for the cell suspension for which lysis treatment was performed beforehand in the same manner as that described Example 1, which was taken as 100%.

The results are shown in FIG. 3. It was revealed that, within a specific concentration range, the lysis ratio was markedly improved with increase of the SDS concentration.

Example 3

Measurement in Milk Sample by Immunochromatographic Method

An immunochromatographic method was performed for a milk sample obtained from a cow with mastitis. The measurement was performed in the same manner as that of Example 2, and the appeared reddish purple line was visually examined (positive +, negative −). The results obtained with lysis treatment solutions containing 1% (final concentration) of Triron X, 0.1 M MOPSO, pH 7.5, and 2.2 mg/ml of lysozyme, and containing or not containing 0.01% SDS (final concentration for the both) were compared. Separately, in order to confirm the number of *Escherichia coli* in the milk, quantification was performed by quantitative PCR. Genomic DNA was extracted from the milk (100 μl) by using DNA Mini Kit (Qiagen), and then PCR was performed by using Quantification of *Escherichia coli* (all strains) (PrimerDesign) to quantify the amount of *Escherichia coli* contained in the milk.

The numbers of *Escherichia coli* calculated by PCR and the determination results obtained by the immunochromatographic method are shown in Table 1. Use of the lysis treatment solution containing lysozyme and SDS enabled detection of *Escherichia coli* in an amount that cannot be measured so far. Since the amount of *Escherichia coli* contained in milk is $10^6$ (cells/ml) or larger in most cases, it was revealed that use of this lysis treatment solution markedly improves the diagnosis sensitivity.

TABLE 1

| Sample No. | Number of *Escherichia coli* (cells/ml) | Result of immunochromatography | |
|---|---|---|---|
| | | Lysozyme without SDS | Lysozyme with SDS |
| 2 | $3 \times 10^5$ | − | + |
| 13 | $5 \times 10^5$ | − | + |
| 24 | $1 \times 10^6$ | − | + |
| 35 | $3 \times 10^6$ | − | + |
| 46 | $4 \times 10^6$ | − | + |
| 57 | $5 \times 10^6$ | + | + |

The invention claimed is:

1. A method for lysing cells of gram-negative coliform bacteria contained in milk, which comprises
   a) mixing a lysis agent containing lysozyme, an ionic surfactant, and a nonionic surfactant with the milk in which the cells of the gram-negative coliform bacteria are existing, and
   b) allowing the lysis agent to lyse the cells of the gram-negative coliform bacteria, and further allowing the lysed cells of the gram-negative coliform bacteria to release a specific substance existing in the inside of the cells of the gram-negative coliform bacteria to the milk, and
   c) collecting the milk containing the specific substance.

2. The lysis method according to claim 1, wherein the ionic surfactant is an anionic surfactant.

3. The lysis method according to claim 2, wherein the anionic surfactant comprises an alkyl sulfate; and/or
   the nonionic surfactant comprises a polyoxyethylene alkyl phenyl ether.

4. The lysis method according to claim 2, wherein, in the step of mixing the lysis agent with the milk to lyse the bacteria existing in the milk, final concentration of the anionic surfactant is not lower than 0.01% and not higher than 0.15%.

5. The lysis method according to claim 4, wherein, in the step of mixing the lysis agent with the milk, final concentration of lysozyme is not lower than 0.1 mg/ml and not higher than 200 mg/ml; and/or
   in the step of mixing the lysis agent with the milk, final concentration of the nonionic surfactant is not lower than 0.03% and not higher than 10%.

6. A method for detecting a specific substance released from cells of gram-negative coliform bacteria contained in milk, which comprises:
   the steps of a), b), and c) defined in claim 1, and further comprises:
   detecting the specific substance released from the inside of the lysed cells of the gram-negative coliform bacteria.

7. The detection method according to claim 6, wherein the detecting step is performed by an immunochromatographic method.

8. The method according to claim 7, wherein the immunochromatographic method comprises: (1) contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) flowing the milk up to the second part or a part existing downstream therefrom to obtain a detectable signal of the label at the second part or a part existing downstream therefrom.

9. The method according to claim 8, wherein the labeled first antibody directed to the specific substance is retained in the first part.

10. The method according to claim 8, wherein the third part is constituted by two or more kinds of members having voids that can remove milk fat globules of different particle sizes, respectively.

11. The method according to claim 10, wherein the third part is constituted by a first member disposed downstream and a second member disposed upstream, and retention particle size of the second member is larger than retention particle size of the first member.

12. The lysis method according to claim 1, wherein the ionic surfactant is sodium dodecylsulfate (SDS).

13. The lysis method according to claim 1, wherein the gram-negative coliform bacteria are *Escherichia coli*, and/or *Klebsiella* bacteria.

* * * * *